United States Patent [19]

Rubino

[11] 3,981,986

[45] Sept. 21, 1976

[54] ZIRCONIUM-ALUMINUM-POLYOL BUFFERED ANTI-PERSPIRANT COMPLEXES

[75] Inventor: Andrew M. Rubino, New Providence, N.J.

[73] Assignee: Armour Pharmaceutical Company, Phoenix, Ariz.

[22] Filed: Jan. 8, 1974

[21] Appl. No.: 431,639

Related U.S. Application Data

[63] Continuation-in-part of Ser. No. 418,712, Nov. 23, 1973.

[52] U.S. Cl. .......... 424/47; 260/429.3; 260/429.9

[51] Int. Cl.[2] .......... A61K 7/00; A61K 9/00; C07F 7/00

[58] Field of Search .......... 424/47, 65, 68; 260/448 R, 429.3, 429.9

[56] References Cited

UNITED STATES PATENTS

| | | | |
|---|---|---|---|
| 2,236,387 | 3/1941 | Wallace, Jr. et al. | 424/68 |
| 2,814,584 | 11/1957 | Daley | 424/66 |
| 2,814,585 | 11/1957 | Daley | 424/66 |
| 2,837,400 | 6/1958 | Barnett | 424/66 X |
| 2,854,382 | 9/1958 | Grad | 424/68 |
| 3,359,169 | 12/1967 | Slater, Jr. et al. | 424/68 |
| 3,407,254 | 10/1968 | Siegal et al. | 424/66 |
| 3,420,932 | 1/1969 | Jones et al. | 424/68 X |
| 3,555,146 | 1/1971 | Jones et al. | 424/66 X |
| 3,792,068 | 2/1974 | Luedders et al. | 424/47 X |

*Primary Examiner*—Helen M. S. Sneed
*Attorney, Agent, or Firm*—Frank T. Barber; William W. Schwarze

[57] ABSTRACT

Water soluble anti-perspirant complexes are provided which comprise a combination of a basic aluminum-polyol compound, a zirconium compound and an organic buffer which may be urea, an amino acid in which the number of amino groups is equal to the number of carboxyl groups in the molecule, an alkaline or hydroxy salt of such amino acid, or mixtures thereof. The various components are present in the complex in amounts such that the Al/Zr mol ratio is about 10:1 to 1:10 and the pH of an aqueous solution containing 5 to 15 weight percent of the complex (based on the oxides of aluminum and zirconium) is at least about 3. The basic aluminum-polyol compounds may be those described in U.S. Pat. Nos. 3,359,169; 3,420,932; 3,405,153 and 3,555,146, particularly basic aluminum chloride-propylene glycol complex. The zirconium compound may be a zirconium oxy (zirconyl) salt and/or zirconium hydroxy salt. Preferred amino acid buffers include glycine and β-alanine and the corresponding salts including the alkaline and alkaline earth glycinates, aluminum dihydroxy or monohydroxy glycinates, and aluminum-magnesium-hydroxy-glycine compounds. The complexes may be used in conventional anti-perspirant forms, including aqueous and/or hydro-alcoholic solutions, powder-in-oil sprays, creams, lotions and sticks.

14 Claims, No Drawings

ZIRCONIUM-ALUMINUM-POLYOL BUFFERED ANTI-PERSPIRANT COMPLEXES

CROSS-REFERENCE TO RELATED APPLICATIONS

This application is a continuation-in-part of my copending application Ser. No. 418,712, filed Nov. 23, 1973, entitled "Aluminum Zirconium Antiperspirant Systems With Salts Of Amino Acids".

BACKGROUND OF THE INVENTION

The present invention relates to aluminum-zirconium-polyol buffered anti-perspirant complexes. More particularly, the invention is directed to water soluble complexes of zirconium which have a sufficiently high pH to be acceptable in anti-perspirant formulations for application to the human axilla.

It has been known in the art for some time that zirconium salts provide exceptionally effective anti-perspirant properties. Such zirconium compounds have included particularly the acidic zirconium salts, such as zirconium oxy chloride or zirconyl chloride, zirconium hydroxy chloride, and other halide and sulfate substitutes of the salts. However, the zirconium salts are extremely acidic and irritating to the skin. For example, a solution of zirconyl chloride which is effective as an anti-perspirant has a pH of only about 0.8 and a solution of zirconyl hydroxy chloride which is effective as an anti-perspirant has a pH of only about 1.2. As a result, it is necessary to buffer these solutions up to a pH which is suitable for application to the human skin, i.e., up to at least about 3 to 5.

A number of prior attempts have been made in the art to buffer solutions of zirconium salts or to form zirconium complexes which take advantage of the effectiveness of zirconium compounds. One early attempt included the development of sodium zirconium lactate for use in cologne-stick type formulations. This lactate complex salt was sufficiently alkaline (pH 8.5), but was ineffective as an anti-perspirant, and was repeatedly implicated in the generation of "zirconium granulomas" in some users.

Other attempts to make use of the acidic zirconium salts involved the buffering of solutions of these salts with urea (see U.S. Pat. No. 2,814,584 to Daley) or water soluble amino acids (see U.S. Pat. Nos. 2,814,585 to Daley and U.S. Pat. No. 2,854,382 to Grad) or aluminum hydroxy halides (see U.S. Pat. No. 2,906,668 to Beekman).

More recently, various derivatives have been formed incorporating zirconium compounds, including the amine-amide derivatives of U.S. Pat. No. 3,407,254 to Siegal et al., and the polyhydroxy derivatives of U.S. Pat. Nos. 3,405,153 and 3,555,146 to Jones and Rubino.

While the above attempts have succeeded in varying degrees in alleviating the acidic characteristics of zirconium salts, an entirely satisfactory zirconium anti-perspirant composition has not been previously found. Thus, it is desired to find a zirconium anti-perspirant composition which effectively makes use of the exceptional anti-perspirant properties of the zirconium, while at the same time offsetting the acidity and other disadvantages of zirconium salts. Moreover, it is desired to have zirconium anti-perspirant systems which are useful in mixtures of water and non-aqueous solvents such as alcohol, particularly for use in hydro-alcoholic aerosol sprays and/or non-aerosol manually pumped sprays.

SUMMARY OF THE INVENTION

According to the present invention, it has been found that effective anti-perspirant compositions may be achieved by forming water soluble complexes which comprise a combination of a basic aluminum-polyol compound, a zirconium compound selected from zirconium oxy salts, zirconium hydroxy salts and mixtures thereof, and an organic buffer selected from the group consisting of urea, amino acids in which the number of amino groups is equal to the number of carboxyl groups in the molecule, alkaline and hydroxy salts of such amino acids, and mixtures thereof. These compounds should be present in the complex in such amounts as to yield an Al/Zr mol ratio of about 10:1 to 1:10, and preferably about 1:1 to 4:1, and should be such as to yield a pH of at least about 3 when the complex is placed in aqueous solution in an amount such that the solution contains about 5 to 15 weight percent of zirconium plus aluminum, calculated as the oxides.

The astringent complexes of the present invention may be obtained in solution or dry powder form. As a result, the complexes are satisfactory for use in any of the wide variety of conventional anti-perspirant forms, including lotions, creams, roll-ons, hydro-alcoholic aerosol sprays, and the presently popular powder-in-oil sprays, as well as manually-pumped hydro-alcoholic sprays.

DETAILED DESCRIPTION OF PREFERRED EMBODIMENTS

As used herein, the term "basic aluminum-polyol compound" refers to complexes of basic aluminum halides, sulphates and sulfamates with polyhydroxy compounds having a carbon chain in which at least two carbon atoms link a hydroxyl group to said chain. Complexes of this type are described, for example, in U.S. Pat Nos. 3,359,169 and 3,420,932, as well as copending U.S. patent application Ser. No. 156,476 of John L. Jones and Andrew M. Rubino entitled "Basic Aluminum Bromide-Polyol Complexes And Methods Of Making Same" now U.S. Pat. No. 3,792,070. The disclosures of each of these patents and patent application are incorporated herein by reference.

In general, these basic aluminum-polyol complexes may be represented by the general formula:

$$Al_2(H_2O)_{y-z}(OH)_{6-nx}(A)_n(R)_z$$

wherein A is selected from the class consisting of chloride, bromide, iodide, sulfate and sulfamate; R is the coordinating moiety of a polyhydroxy compound having a carbon chain in which at least two carbon atoms link a hydroxyl group to said chain, $n$ is a positive integer of from 1 to 4; $x$ is the valence of A, $y$ has a value of about 0.5 to 6 and is always such that $(y-z)$ does not give a negative value; and $z$ is the number of available coordination sites, with nx being from 1 to 4.

Suitable polyhydroxy compounds for use in the above formula include: propylene glycol; 1,1,1-trimethylol propane; 1,3-butylene glycol (1,3-butane-diol); glycerine (1,2,3-trihydroxy propane); 2-methyl-2,4-pentane-diol; neopentyl glycol (2,2-dimethyl-1,3-dihydroxy pentane); polyethylene glycol (mol. wt. = 400); Polyglycol 15-200 (a Dow material having an ethereal linkage between propylene oxide and ethylene and condensed with glycerine in which each chain has a terminal hydroxy group (mol. wt. = 2700); p-xylene α,α diol; butyne-1,4 diol; 2-ethyl-1,3-hexane-diol; and polypropylene glycol (av. mol. wt. = 400).

Particularly preferred polyhydroxy complexes of the above formula for use in the present invention are those prepared from basic aluminum chlorides and propylene glycol and having the formula:

$$Al_2(H_2O)_{0.7-1.1}(OH)_{4.9-5.1}(Cl)_{0.9-1.1}(1{,}2\ \text{propylene glycol})_{0.7-1.3}$$

In the above formula, the 1,2 propylene glycol may be present in the complex in a number of ways, namely with both carbinol hydrogen atoms being lost by condensation or neutralization, or with only one carbinol hydrogen atom being lost by condensation or neutralization, or with both hydroxy groups remaining intact and coordinated and/or chelated to one of the aluminum atoms. The above preferred complexes are commercially available from Reheis Chemical Company, a division of Armour Pharmaceutical Company, under the trademark "Rehydrol".

It will be understood that the complexes of the above formula may vary in water content from a low range of about 1 to 10 weight percent by Karl Fischer analysis, as indicated in U.S. Pat. No. 3,420,932, up to a high range of about 10 to 17 weight percent water by Karl Fischer analysis, as indicated in U.S. Pat. No. 3,792,070. Similarly, the polyol content may vary from a low range of about 5 to 18 weight percent as indicated in U.S. Pat. No. 3,792,070, to greater than 18 weight percent as indicated in U.S. Pat. No. 3,420,932.

In addition to the complexes of the above general formula for polyhydroxy complexes of basic aluminum salts, the term "basic aluminum-polyol compound" as used herein is also intended to include polyhydroxy derivatives of zinc and zirconium complexes of basic aluminum halides, and mixtures of these derivatives with the previously described polyhydroxy complexes of basic aluminum salts.

These polyhydroxy derivatives which are suitable for use in the present invention are fully described in U.S. Pat. Nos. 3,405,153 and 3,555,146 to Jones and Rubino, the disclosures of which are incorporated herein by reference. These alcohol soluble inorganic-organic complexes may be defined by the general formula:

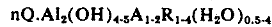

$$nQ.Al_2(OH)_{4-5}A_{1-2}R_{1-4}(H_2O)_{0.5-4}$$

wherein Q is a member of the group consisting of zinc chloride, zinc iodide, zinc bromide, zinc hydroxy chloride, zinc hydroxy iodide, zinc hydroxy bromide, zirconyl chloride, zirconyl bromide, zirconyl iodide, zirconyl hydroxy bromide, zirconyl hydroxy iodide, and zirconyl hydroxy chloride; A is an anion selected from the group consisting of chloride, bromide and iodide; R is the coordinating moiety of a polyhydroxy compound having at least two carbon atoms to which are attached at least two hydroxy groups, and $n$ is the number of moles of Q and is at least 0.05. The polyhydroxy compounds (R) used in the above formula may be selected from the same list as that given above for the polyhydroxy complexes of basic aluminum salts.

The zirconium compounds which are useful in forming the complexes of the present invention include both the zirconium oxy salts and zirconium hydroxy salts, also referred to as the zirconyl salts and zirconyl hydroxy salts. These compounds may be represented by the following general empirical formula:

$$ZrO(OH)_{2-nz}B_z$$

wherein $z$ may vary from about 0.9 to 2 and need not be an integer, $n$ is the valence of B, $2-nz$ is greater than or equal to 0, and B may be selected from the group consisting of halides, nitrate, sulfamate, sulfate and mixtures thereof.

It will be understood that the above formula is greatly simplified and is intended to represent and include compounds having coordinated and/or bound water in various quantities, as well as polymers, mixtures and complexes of the above. As will be seen from the above formula, the zirconium hydroxy salts actually represent a range of compounds having various amounts of the hydroxyl group, varying from about 1.1 to only slightly greater than 0 groups per molecule.

Particularly preferred zirconium compounds for use in the present invention include zirconyl chloride (also referred to as basic zirconium chloride or zirconium oxy chloride) and zirconyl hydroxy chloride, which may be represented by the simple formulas $ZrO\,Cl_2$ and $ZrO(OH)Cl$, respectively. These compounds are commercially available in solution form. In the alternative, the zirconium compounds can be made by dissolution of commercially available zirconium carbonate paste (carbonated hydrous zirconia) in the appropriate amount of the acid of the anion to be used, e.g., hydrochloric acid. Other useful zirconium salts will be apparent to those of ordinary skill in the art, such as trioxodizirconium hydroxy halides and similar salts described in U.S. Pat. No. 2,837,400 to Blumenthal, for example.

The organic buffers which are useful in forming the complexes of the present invention include urea and the so-called neutral amino acids, i.e., amino acids in which the number of amino groups is equal to the number of carboxyl groups in the molecule. Urea has been previously disclosed as a buffer in aqueous zirconium containing anti-perspirant systems in U.S. Pat. No. 2,814,584 to Daley, and neutral amino acids have previously been disclosed as buffers in aqueous zirconium containing anti-perspirant systems in U.S. Pat. No. 2,814,585 to Daley and U.S. Pat. No. 2,854,382 to Grad, all of these patents being assigned to The Proctor & Gamble Company. The disclosures of each of these patents are incorporated herein by reference.

Particularly preferred organic buffers useful in preparing the complexes of the present invention include both alkaline and hydroxy salts of the above referred to amino acids. It is important to note that insoluble as well as soluble salts may be used, in contradistinction to the teachings of U.S. Pat. Nos. 2,814,585 and 2,854,382 to Daley and Grad, respectively, which indicate that only amino acids which are sufficiently soluble in aqueous solution can be used to buffer zirconium anti-perspirant solutions. This phenomenon may be accounted for by the belief that the salts of amino acids, even if insoluble in water, form complexes with the zirconium compounds and basic aluminum compounds, which complexes are soluble in water. Moreover, since the complexes of the present invention may be dried to a solid powder form, it is not necessary that the complexes of the present invention be stable in solution for any great length of time, except when it is desired to redissolve the powder for use in solution form.

Among the salts of amino acids which may be used in the present invention are those derived from the so-called neutral amino acids, i.e., amino acids in which the number of amino groups is equal to the number of carboxyl groups in the molecule. Examples of such amino acids include glycine, DL-valine, $\beta$-alanine, arginine and L-(-)-proline and mixtures thereof. The corresponding salts are the glycinates, DL-valinates, $\beta$-alaninates, argininates and L-(-)-prolinates. Suitable salts of other amino acids useful in the present invention will be evident to those of ordinary skill in the art in view of this specification.

The particular salts of amino acids which may be used include both alkaline and hydroxy salts. As used herein, the term "alkaline" as applied to salts of amino acids is not intended to be limited to those having a pH greater than 7.0, since some complex or not perfectly neutralized salts may have pH's less than 7.0 (e.g., 6.0 or 6.5) and still be useful in this invention. Instead, "alkaline" is merely meant to refer to the usual alkali and alkaline earth cations, including ammonium. For example, suitable alkaline salts include sodium, potassium, ammonium, magnesium and calcium salts of the above-mentioned amino acids. These salts may be obtained commercially or prepared by reacting the particular amino acid in aqueous solution with the carbonate or hydroxide of the particular alkali or alkaline earth metal.

Suitable hydroxy salts of amino acids which may be used in the present invention include the dihydroxy and monohydroxy aluminum salts of amino acids and the so-called aluminum-magnesium-hydroxy-glycine compounds. Essentially, these hydroxy salts are the reaction products of aluminum hydroxy antacids with the appropriate amino salt. For example, the dihydroxy and monohydroxy aluminum salts may be obtained commercially or prepared by reacting the amino acid with aluminum hydroxide ($Al(OH)_3$) powder in aqueous solution with agitation.

Similarly, the desired amino acid may be reacted with the glycine stabilized aluminum hydroxide-magnesium antacid compositions described in U.S. Pat. No. 3,208,906 to Beekman. For convenience, these antacids will be referred to as aluminum-magnesium-hydroxy-glycine compounds. Examples of such compounds, all of which are insoluble in water, include the following:

$Al(OH)_3$-$Mg(OH)_2$ - glycine $Al(OH)_3$-$Mg\ CO_3$ - glycine

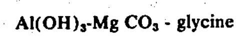

$Al(OH)_3$-$Mg\ Si_3\ O_8$ - glycine

Particularly preferred amino compounds for use in the present invention include dihydroxy aluminum glycinate ($Al(OH)_2\ OOC.CH_2.NH_2$, monohydroxy aluminum glycinate ($Al(OH)(OOC.CH_2NH_2)_2$, which are commercially available from Chattem Chemical Co. and K and K Laboratories, Inc., as well as magnesium glycinate ($Mg(OOC.CH_2.NH_2)_2$) and calcium glycinate ($Ca(OOC.CH_2NH_2)_2$). Commercial glycinates of the above form are available in a large range of different basicities. Accordingly, the amount of glycinate or other salt of amino acid which is necessary to form a complex having a pH in aqueous solution of at least about 3 will depend upon the particular basicity of the amino salt.

Among the advantages of the complexes of the present invention derived from the amino acid salts or derivatives is that they are more basic and better buffers than the simple amino acid complexes themselves. This is due to the fact that most of the derivatives of alkali and alkaline earth metals, particularly those which are insoluble in water, are hydroxylated. Since the formation of complexes of the present invention results in increasing the pH of the higher acid zirconium systems, the more basic amino acid salts and derivatives can be used in smaller amounts to achieve the necessary pH levels for anti-perspirant use. In addition, as a result of using the amino acid salts and derivatives, other ions known for their anti-perspirant activity as well as their basic character are introduced into the astringent complexes of the present invention. For example, the use of dihydroxy aluminum glycinate results in the addition of more aluminum which is well known for its anti-perspirant activity. Furthermore, the presence of polyol moieties renders the zirconium-aluminum systems more amenable or conducive to buffering the pH upward without causing precipitation of the metals.

The particular amounts of each of the compounds to be added to form the complexes of the present invention may vary over a large range, depending upon the particular properties desired.

In general, the relative amounts of basic aluminum compound and zirconium compound to be added should be such as to yield an Al/Zr mol ratio of between about 10:1 and 1:10, and preferably about 1:1 to 4:1. Although greater amounts of zirconium would be desirable in the complex from the standpoint of anti-perspirant efficacy, it will be appreciated that zirconium is considerably more expensive than aluminum. In addition, the greater the amounts of zirconium in the complex, the greater the chance of skin irritation, and the greater the amount of the organic buffer which must be added to obtain a satisfactory pH.

The amount of the organic buffer (amino compound) to be added will also vary greatly depending upon the Al/Zr ratio, the particular organic buffer used, and the pH range which is desired for the particular astringent complex. In general, sufficient amino compound should be added so that the pH of an aqueous solution of the complex at the normal concentrations for anti-perspirant use will be at least about 3, and preferably in the range of about 3 to 5. The usual concentration of the complexes of the present invention for anti-perspirant use will be such that a solution contains a total aluminum plus zirconium concentration of about 5 to 15 weight percent, with the aluminum and zirconium being calculated as the oxides (i.e., $ZrO_2$ and $Al_2O_3$).

If desired, the pH or the concentration of aluminum in the complexes of the present invention may be adjusted by adding aluminum hydroxide powder ($Al(OH)_3$) or aluminum chloride ($AlCl_3$) to the reaction mixture in the formation of the complexes of the present invention. Aluminum chloride, although quite acidic in solution, is well known for its anti-perspirant efficacy.

Similarly, basic aluminum salts, which have been known to the anti-perspirant art for some time, may also be added to the complexes of the present invention, if desired. These basic aluminum salts may be represented by the following general empirical formula:

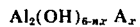

$Al_2(OH)_{6-nx} A_x$ wherein $x$ may vary from greater than 0 to less than 6, $6-nx$ is greater than or equal to 0, $n$ is the valence of $A$, and $A$ is selected from the group consisting of halides, nitrate, sulfamate, sulfate and mixtures thereof. It will of course be understood that the above formula is greatly simplified and is intended to represent and include basic aluminum compounds containing coordinated and/or bound molecules of water as well as polymers, complexes and mixtures of the above basic formula. Particularly useful are the 5/6 basic aluminum chlorides.

The method of forming the complexes of the present invention is not particularly critical. In general, the complexes may be formed simply by adding the various components together in an aqueous solution and then, if desired, drying the solution to a dry powder. The various components are preferably added one at a time with stirring, and moderate heating, such as to a maximum of about 75° or 85° C. for up to a half hour may be advantageous after addition of certain ingredients, particularly when an insoluble compound is added or when a precipitate is formed after the addition of an ingredient. Where a water insoluble amino compound is being used, it is preferable to add this last.

The drying step is not particularly critical and may be carried out in a number of different ways, including vacuum drying, oven drying, spray drying or freeze drying. It will be understood that drying does not mean that all of the water is removed, since a certain amount of water should remain in the complex as coordinated and/or bound water. Thus, drying to just past the point where the solution becomes a friable solid should be sufficient. If the complex is over dried, so that some of the coordinated and/or bound water is removed, the stability and/or activity of the complex may be interferred with, and the complex may not be readily redissolvable in solvents, particularly hydroalcoholic solvents. In some cases, uncontrolled dehydration of the complex can result in a diminution or impairment of both its solubility in hydro-alcoholic systems and the compatibility of such solutions with halohydrocarbon propellants in aerosol formulations, for example.

While it has been indicated that the reaction process is not considered particularly critical, it will be understood that sufficient time, heat and agitation are needed to allow reaction of the salts to form the new complexes of the present invention. This is particularly so in the case of insoluble amino acid salts which may be used to form complexes of this invention. Although I do not wish to be bound by any particular theory, it is believed that there is a continuation of the reaction during the drying of the solution to a solid powder. Thus, the pH of a reconstituted solution is often higher than might otherwise be expected from the pH of the solution before drying, even taking into consideration different solution concentrations.

The complexes of the present invention will now be illustrated in more detail with reference to the following specific, non-limiting examples:

EXAMPLE I

Five grams of Rehydrol powder (19.9% Al) was dissolved in 10 grams of water and then added to 94 grams of a 30% zirconyl chloride aqueous solution (13.6% Zr) with agitation. The solution was buffered and stabilized by dissolving 30 grams of $\beta$-alanine in the above mixture. After tray drying the solution at 65° C. under a vacuum of 252 mm of Hg the product was found to contain 1.6% Al, 20.1% Zr, 3.8% propylene glycol, 17.1% Cl, and 47.1% $\beta$-alanine.

EXAMPLE II

Ten grams of Rehydrol (19.9% Al) was dissolved in 20 grams of water. To this solution was added 2 grams of L-(-)-proline and 8.05 grams of 33⅓% zirconyl hydroxychloride (14.1% Zr) with agitation. The resulting solution was evaporated at 60° C. under a vacuum of 303 mm of Hg. The product contained 14.7% Al, 7.99% Zr, 13.6% Cl, 17.3% propylene glycol, and 11% proline.

EXAMPLE III

To 50 grams of water was added 14.4 grams of zinc chloride, with stirring until a clear solution resulted. To the above was added 22 grams of a 50% aluminum chlorhydroxide solution (12.4% Al) and 18 grams of propylene glycol with agitation (see U.S. Pat. No. 3,405,153). After five minutes of stirring 6.7 grams of a 30% zirconyl chloride aqueous solution (13.6% Zr) was added and the entire solution buffered to a pH of 3.3 with 5 grams of glycine. On tray drying at 65° C. under a vacuum of 175 mm of Hg, the product was found to contain 18.8% Zr, 6.74% Al, 26.4% Cl, 15.7% propylene glycol, 2.82% Zr and 14.3% glycine.

EXAMPLE IV

Fifteen grams of Rehydrol (19.9% Al) was dissolved in 20 grams of water. To this was added 11.4 grams of a 30% zirconyl chloride solution (13.6% Zr) and then the entire mixture was buffered up to a pH of 3.9 with 4 grams of urea and 2 grams of aluminum hydroxide powder (28.8% Al) by agitating the mixture at 80° C. until a clear solution resulted. After tray drying the solution at 50° C. under a vacuum of 303 mm of Hg, the product was found to contain 15.2% Al, 6.2% Zr, 17.1% urea, 19.3% propylene glycol and 13.9% Cl.

EXAMPLE V

Five grans of Rehydrol powder (19.9% Al) was dissolved in 10 grams of water. To this was added 2 grams of glycine with stirring until a clear solution resulted. To the above was added 270 grams of a zirconyl iodide solution, $ZrOI_2$ (6.3% Zr) and then 2.5 grams of aluminum hydroxide powder (28.8% Al) while agitating at 85° C. for 30 minutes. The addition of 38 grams of glycine to the resultant clear solution buffered the mixture from a pH of 2.2 to 2.8. The product was evaporated at 85° C. under a vacuum of 150 mm of Hg. The material analyzed 1.4% Al, 13.5% Zr, 4.68% propylene glycol, 0.69% Cl, 39.9% I, and 32.4% glycine.

EXAMPLE VI

Magnesium glycinate was prepared by reacting 2 grams of glycine with 1.2 grams of basic magnesium carbonate (26.3% Mg) in 20 grams of water. The mixture was heated at 70° C. with agitation for 15 minutes and then cooled. Forty grams of Rehydrol powder (19.9% Al) was then dissolved in 100 grams of water. To this solution was added 32.4 grams of 33⅓% zirconyl hydroxychloride (14.1% Zr). Addition of the magnesium glycinate slurry to the above mixture while heating at 85° C. for 20 minutes with agitation resulted in a clear solution. The solution was evaporated at 60° C. under a vacuum of 303 mm Hg. The product contained 16.1% Al, 9.49% Zr, 14.8% Cl, 16.6% propylene glycol, 0.82% Mg, and 3.63% glycine.

EXAMPLE VII

Sodium β-alaninate was prepared by mixing 2 grams of β-alanine and 1.79 grams of 50% sodium hydroxide in 20 grams of water at 80° C. for 15 minutes. Ten grams of Rehydrol powder (19.9% Al) was then dissolved in 50 grams of water. To this was added 4.1 grams of a zirconyl chloride solution (13.6% Zr). The sodium β-alaninate solution was added to the above mixture with agitation at 80° C. A precipitate formed which partially dissolved after 15 minutes of heating. The addition of 12.2 grams more of the zirconyl chloride solution completely redissolved the precipitate after an additional 15 minutes of agitation at 80° C. The solution was evaporated at 70° C. under a vacuum of 252 mm of Hg. The product contained 17.1% Al, 5.14% Zr, 22.1% propylene glycol, 15.9% Cl, 2.86% Na, and 4.24% β-alanine.

EXAMPLE VIII

Ten grams of Rehydrol powder (19.9% Al) was dissolved in 20 grams of water. To 90.8 grams of a 30% zirconyl chloride solution (13.6% Zr) was added 10 grams of dihydroxyaluminum glycinate (from Chattem Chemical Co., 16.8% Al, 48.7% glycine) while agitating at 75° C. for 20 minutes. The above mixture was added to the Rehydrol solution with stirring. The final solution was oven dried at 55° C. under a vacuum of 303 mm of Hg. The product contained 6.7% Al, 23.0% Zr, 8.9% glycine, and 20.4% Cl.

EXAMPLE IX

Four grams of dihydroxyaluminum glycinate (from K and K Chemical Co., 17.3% Al, 45.7% glycine) was added to 91.5 grams of 33⅓% zirconyl hydroxychloride (14.1% Zr) while agitating at 75° C. until a clear solution was obtained. The resultant solution was added to 25 grams of a 20% Rehydrol solution (4% Al) with agitation. The material was evaporated at 75° C. under a vacuum of 125 mm of Hg. The product contained 4.49% Al, 33.3% Zr, 3.7% propylene glycol, 4.69% glycine and 14.9% Cl.

EXAMPLE X

Calcium argininate was prepared by dissolving 44 grams of L-(+)-arginine in 300 grams of water. To this solution was added 12.1 grams of calcium carbonate powder while agitating at 75° C. for one half hour. To 30 grams of a 33⅓% Rehydrol solution (6.7% Al) was added 294 grams of a 30% zirconyl chloride solution (13.6% Zr) and to this solution was added the calcium argininate mixture with agitation at 50° C. The heating was continued until a clear solution resulted, which was then evaporated at 55° C. under a vacuum of 303 mm of Hg. The product contained 1.44% Al, 25.7% Zr, 21.4% Cl, 2.8% propylene glycol, 3.2% Ca and 27.3% arginine.

As indicated previously, the complexes of the present invention may be used in a variety of conventional anti-perspirant forms which are applied to the human axilla for effective perspiration inhibition. In such formulations, the complex should be present in such amounts that the total aluminum plus zirconium content of the formulation is between about 1.5 and 15 weight percent (depending on the type of formulation employed), calculated as the oxides of the aluminum and zirconium.

For example, aqueous or hydro-alcoholic (e.g. 50% ethanol — 50% water) solutions of the complexes may be used in lotions, oil/water creams, and co-dispensing aerosols. In either the aqueous solutions or the hydro-alcoholic solvents, the complexes of the present invention should be present in the above anti-perspirant forms in amounts such that the total content of aluminum plus zirconium in the formulation is on the order of about 5 to 15 weight percent (calculated as the oxides of aluminum and zirconium) or 10 to 30 weight percent of the active ingredient (calculated on a solids basis). When used in a hydro-alcoholic aerosol system the complex powder should comprise about 5 to 15 weight percent of the anti-perspirant formulation.

The complexes of the present invention may also be used in the now popular powder-in-oil aerosol sprays. The powder-in-oil systems comprise the dispersion of a finely divided anti-perspirant powder, such as the dried complexes of the present invention, in a non-solubilizing polar organic liquid such as an ester which serves as both a dispersion medium as well as an emollient. The organic liquid coats or wets the powder particles to render them heavier and more occlusive and/or substantive to the axillary region. This primary powder-in-oil suspension, known as the "concentrate", may also include a suspending or anti-compaction agent such as Cab-O-Sil or Bentone 34, to inhibit the dispersed phase from settling and compacting irreversibly. The so-called "extra-dry" formulations use less emollient and higher levels of dry powder, such as talc. Finally, after dynamic agitation the viscous concentrate is generally mixed with about 9 times its weight of a blend of standard propellants.

When used in the powder-in-oil aerosol sprays, the complexes of the present invention should be present in the finished formulation to the extent of about 1 to 6 weight percent, and preferably about 1.5 to 3 weight percent, total aluminum plus zirconium, calculated as the oxides. A typical powder-in-oil aerosol suspension would employ about 5 percent w/w of the active ingredient (dried complex) or about 2.5 percent total oxides.

Typical anti-perspirant formulations employing the complexes of the present invention are exemplified in Table I.

The present invention may be embodied in other specific forms without departing from the spirit or essential attributes thereof and, accordingly, reference should be made to the appended claims, rather than to the foregoing specification as indicating the scope of the invention.

TABLE I

ANTIPERSPIRANT FORMULATIONS

| Ingredient | A* Powder-in-oil aerosol | B* Powder-in-oil extra-dry aerosol | Parts by Weight C Spray: (Manual-Pump) | D Oil-in-water lotion | E Oil-in-water cream |
|---|---|---|---|---|---|
| Active Ingredient (Antiperspirant) | | | | | |
| Complex of Example II | 3.5 | | | | |
| Complex of Example IV | | | 10.0 | | |
| Complex of Example III | | 5.0 | | | |
| Complex of Example VI | | | | 18.0 | 15.0 |
| Isopropyl Myristate | 6.0 | 3.0 | | | |
| Cab-O-Sil M-5 (1) | 0.3 | 0.5 | | | |
| Perfume | 0.2 | | 0.5 | q.s. | q.s. |
| Propylene Glycol | | | 15.0 | | |
| Propellant 11 (trichlorofluoromethane) | 45.0 | 45.0 | | | |
| Propellant 12 (dichlorodifluoromethane) | 45.0 | 45.0 | | | |
| Water | | | 19.5 | 66.0 | 56.0 |
| Alcohol SD-39C | | | 55.0 | | |
| Talc, U.S.P. | | 1.5 | | | |
| Arlacel 165 (4) | | | | | 18.0 |
| Amerchol L-101 (2) | | | | 5.0 | |
| Solulan 98 (2) | | | | 2.0 | |
| Myrj 52 (4) | | | | 4.0 | |
| Cetyl Alcohol | | | | 2.0 | |
| Glycerin | | | | 2.0 | 5.0 |
| Veegum HV (3) | | | | 1.0 | |
| Preservative | | | | q.s. | q.s. |
| Spermaceti | | | | | 5.0 |
| Titanium Dioxide | | | | | 1.0 |

(1) Cab-O-Sil M-5 — fumed amorphous silica of Cabot Corp.
(2) Amerchol L-101 and Solulan 98 — lanolin derivatives of Amerchol, Inc.
(3) Veegum HV — product of R. T. Vanderbilt & Co.
(4) Arlacel 165 and Myrj 52 — non-ionic emulsifiers of ICI America, Atlas Chem., Div.
*For "powder-in-oil" aerosols, active ingredient powders are ground before use in a micronizer to yield powders containing a particle size greater than 97% through a 325 mesh screen (44u).

I claim:

1. An astringent, water soluble complex formed by reacting in an aqueous medium:

a. a basic aluminum-polyol compound, selected from the group consisting of complexes having the following general empirical formulas:

$$Al_2(H_2O)_{y-z}(OH)_{6-nx}(A)_n(R)_z \quad (1)$$

wherein A is selected from the group consisting of chloride, bromide, iodide, sulfate and sulfamate; R is the coordinating moiety of a polyhydroxy compound having a carbon chain in which at least two carbon atoms link a hydroxyl group to said chain; $n$ is a positive integer of from 1 to 4; $x$ is the valence of $A$, $y$ has a value of about 0.5 to 6 and is always such that $(y-z)$ does not give a negative value; and $z$ is the number of available coordination sites, with $nx$ being from 1 to 4, $$nQ.Al_2(OH)_{4\text{-}5}A_{1\text{-}2}R_{1\text{-}4}(H_2O)_{0.5\text{-}4}$$

wherein $Q$ is selected from the group consisting of zinc chloride, zinc iodide, zinc bromide, zinc hydroxy chloride, zinc hydroxy iodide, zinc hydroxy bromide, zirconyl chloride, zirconyl bromide, zirconyl iodide, zirconyl hydroxy bromide, zirconyl hydroxy iodide and zirconyl hydroxy chloride; $A$ is an anion selected from the group consisting of chloride, bromide and iodide; $R$ is the coordinating moiety of a polyhydroxy compound having at least two carbon atoms to which are attached at least two hydroxy groups, and $n$ is the number of moles of $Q$ and is at least 0.05, and mixtures of (1) and (2);

b. a zirconium compound selected from trioxodizirconium salts and the group having the general empirical formula:

$$ZrO(OH)_{2-nz}B_z$$

wherein $z$ may vary from 0.9 to 2, $n$ is the valence of B, $2-nz$ is greater than or equal to 0, and $B$ is selected from the group consisting of halide, nitrate, sulfamate, sulfate and mixtures thereof; and c. an organic buffer selected from the group consisting of urea, an amino acid in which the number of amino groups is equal to the number of carboxyl groups in the molecule, an alkaline salt of said amino acids, hydroxy aluminum salt of said amino acid, and mixtures thereof, said zirconium and basic aluminum-polyol compounds being present in such amounts as to yield an Al/Zr mole ratio of about 10:1 to 1:10, and said organic buffer being present in such an amount that the pH of a 5 to 15 weight percent (based on the oxides of Al and Zr) aqueous solution of the complex is at least about 3;

and drying the reaction mixture to a friable solid which is said complex.

2. An astringent complex according to claim 1 wherein said basic aluminum-polyol compound has the general empirical formula:

$$Al_2(H_2O)_{0.7\text{-}1.1}(OH)_{4.9\text{-}5.1}(Cl)_{0.9\text{-}1.1}(1,2\text{ propylene glycol})_{0.7\text{-}1.3}.$$

3. An astringent complex according to claim 1 wherein B is chloride and z in said zirconium compound is about 1.

4. An astringent complex according to claim 1 wherein B is chloride and z in said zirconium compound is about 2.

5. An astringent complex according to claim 1 wherein said organic buffer is an amino acid selected from the group consisting of glycine, dl-tryptophane, dl- β-phenyl-alanine, dl-valine, dl-methionine, β-alanine, and mixtures thereof.

6. An astringent complex according to claim 1 wherein said organic buffer is an alkaline salt or a hydroxy aluminum salt of an amino acid and said salt is derived from an amino acid selected from the group consisting of glycine, β-alanine, DL-valine, arginine, L-(-)-proline, and mixtures thereof.

7. An astringent complex according to claim 6 wherein said organic buffer is an alkaline salt in which the cation is selected from the group consisting of sodium, potassium, ammonium, magnesium, calcium and mixtures thereof.

8. An astringent complex according to claim 6 wherein said organic buffer is a hydroxy aluminum salt selected from the group consisting of dihydroxy aluminum glycinate, monohydroxy aluminum glycinate, aluminum-magnesium-hydroxy-glycine compounds, and mixtures thereof.

9. An astringent complex according to claim 1 wherein said complex also includes a basic aluminum compound having the general empirical formula:

$$Al_2(OH)_xA_{6-x}$$

wherein $x$ may vary from greater than 0 to less than 6, and $A$ is selected from the group consisting of halide, nitrate, phenolsulfonate, sulfamate, sulfate and mixtures thereof.

10. An astringent complex according to claim 1 wherein the Al/Zr mol ratio is about 1:1 to 4:1.

11. An astringent complex according to claim 1 wherein said complex also includes aluminum chloride.

12. An aerosol anti-perspirant composition comprising an aerosol propellant, water, ethanol, and the complex according to claim 1, wherein said complex is present in an amount of about 5 to 15 weight percent of the anti-perspirant composition.

13. A powder-in-oil anti-perspirant composition comprising an aerosol propellant, a non-solubilizing polar organic liquid dispersion medium for the powdered complex, and the complex according to claim 1 wherein said complex is present in an amount of about 1–6 weight percent of the anti-perspirant composition.

14. An anti-perspirant composition comprising an aqueous solution of the complex according to claim 1 wherein said complex is present in an amount such that the total amount of aluminum plus zirconium in the solution, calculated as the oxides, is about 5 to 15 weight percent.

* * * * *